United States Patent [19]

Warkentin et al.

[11] 4,009,276
[45] Feb. 22, 1977

[54] OXADIAZOLINE DERIVATIVES

[75] Inventors: John Warkentin, Burlington; Kottieth Ramakrishnan, Hamilton; Rup C. Jain; Frank W. Wandelmaier, both of Montreal, all of Canada

[73] Assignee: Canadian Patents and Development Limited, Ottawa, Canada

[22] Filed: Nov. 3, 1975

[21] Appl. No.: 628,223

[52] U.S. Cl. ............................ 424/272; 260/240 G; 260/307 G
[51] Int. Cl.² .................................... C07D 271/06
[58] Field of Search ................. 260/240 G, 307 G; 424/272

[56] References Cited
UNITED STATES PATENTS

| | | |
|---|---|---|
| 3,417,082 | 12/1968 | Taylor .......................... 260/240 G |
| 3,784,555 | 1/1974 | Cebalo et al. .................. 260/240 G |

*Primary Examiner*—Arthur P. Demers
*Attorney, Agent, or Firm*—Alan A. Thomson

[57] ABSTRACT

Benzylidenehydrazono-oxadiazoline compounds have been prepared of the formula:

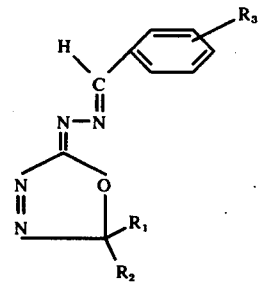

wherein $R_1$ and $R_2$ are both lower alkyl or form with the heterocyclic ring carbon atom an alicyclic ring; and $R_3$ when present is selected from halogen, lower alkyl and lower alkoxy. The preparation involves condensing a benzaldehyde with carbodihydrazide and further condensing with a ketone (or vice versa) to form the corresponding crossed carbodihydrazone, and oxidizing and cyclizing to form the oxadiazoline derivatives. These derivatives have analgesic and/or anti-inflammatory activity.

10 Claims, No Drawings

OXADIAZOLINE DERIVATIVES

FIELD OF THE INVENTION

This invention is concerned with certain benzylidenehydrazono-oxadiazoline compounds and a method of preparing these compounds. The compounds have biological activity. Typical compounds within the scope of the invention are 5,5-Dialkyl-2-(benzylidenehydrazono)-$\Delta^3$-1,3,4-oxadiazoline where the benzene ring may be further substituted with alkyl, alkoxy or halogen groups, and where the 5,5-dialkyl groups may form part of an alicyclic spiro ring.

DESCRIPTION OF THE PRIOR ART

The compound 2-imino-$\Delta^3$-1,3,4-oxadiazoline with the Z-configuration at the exocyclic double bond has recently been reported. One diaryl (derived from benzophenone) hydrazono-oxadiazoline has also been prepared by an oxidative cyclication of the corresponding carbohydrazone. No biological activity has been known for these compounds.

SUMMARY OF THE INVENTION

We have now found that certain benzylidenehydrazono-oxadiazoline compounds can be prepared having the formula:

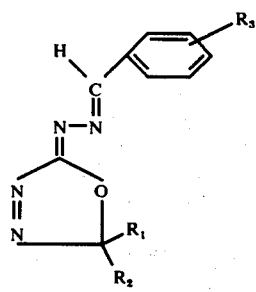

wherein $R_1$ and $R_2$ are both lower alkyl or both form with the heterocyclic ring carbon atom a spirocyclic ring; and $R_3$ when present is selected from halogen, lower alkyl and lower alkoxy. $R_1$ and $R_2$ are selected from the group consisting of methyl, ethyl and propyl, and spiro rings formed with the 5-carbon atom such as cyclopentyl and cyclohexyl. $R_3$ need not be present, but when present is selected from methyl, ethyl and propyl, methoxy etc, chloro, fluoro and bromo, and may be located at any position on the benzene ring. These compounds have been found to have analgesic and/or anti-inflammatory activity in animal tests.

The compounds may be conveniently prepared by (a) condensing one of (i) an aldehyde of the formula

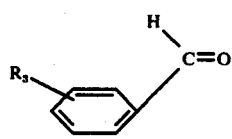

and (ii) a ketone of the formula

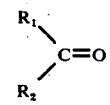

with carbodihydrazide in approximately equimolar amounts, and further condensing the product with the other of (i) and (ii) to form the carbodihydrazone

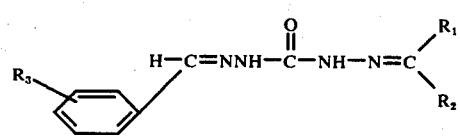

and (b) oxidizing and cyclizing this carbodihydrazone to form oxadiazoline derivatives. It is preferred to condense the aldehyde first in step (a) in approximately equimolar amounts with the carbodihydrazide, and then use excess of the ketone in the subsequent condensation. In step (b) it is preferred to have present an oxidative cyclizing agent comprised of lead tetraacetate, but other mild oxidizing reagents known in the art as equivalent may be used.

EXAMPLES AND PREFERRED EMBODIMENTS

The following example is illustrative.

EXAMPLE 1

A 4-Aminosemicarbazones p-Chlorobenzaldehyde-4-aminosemicarbazone was prepared as follows:

Carbohydrazide (5.04 g, 0.056 mol) and p-chlorobenzaldehyde (5.6 g, 0.040 mol) in 50 ml of absolute ethanol were heated at the reflux temperature for three hours. Ethanol (20 ml) and water (10 ml) were added and the resulting mixture was refluxed for 30 minutes more. Cooling with ice precipitated a white powder which was filtered off, washed with hot water (50 ml) and dried. The yield of white product, m.p. 188° to 189° C, was 6.28 g (74%).

Similarly for analogous derivatives:

p-Fluorobenzaldehyde-4-aminosemicarbazone colorless crystals, m.p. 182° to 184°, 81.6% yield.

m-Fluorobenzaldehyde-4-aminosemicarbazone cream colored crystals, m.p. 181° to 182°, 88% yield.

o-Fluorobenzaldehyde-4-aminosemicarbazone colorless needles, m.p. 184° to 186°, 85.2% yield.

B Carbohydrazones

Crossed carbohydrazone of acetone and p-chlorobenzaldehyde was prepared as follows:

p-Chlorobenzaldehyde-4-aminosemicarbazone (5.95 g, 0.028 mol) in acetone (200 ml) was heated for 24 hours at the reflux temperature. Cooling, evaporation of the excess acetone with a rotary evaporator, addition of petroleum ether (100 ml, b.p. 30° to 60°) heating to the boiling point and cooling gave a white precipitate which was filtered off and washed with petroleum ether. The yield of dry, white product, m.p. 164° to 165°, was 5.9 g (83%).

Similarly for analogous derivatives:

Crossed carbohydrazone of acetone and p-fluorobenzaldehyde:white powder, m.p. 156° to 158°, 83.5% yield.

Crossed carbohydrazone of acetone and m-fluorobenzaldehyde:white powder, m.p. 184° to 185°, 83.3% yield.

Crossed carbohydrazone of acetone and o-fluorobenzealdehyde:white powder, m.p. 152° to 153°, 81.2% yield.

C Oxadiazolines 5,5-Dimethyl-2-(p-chlorobenzylidenehydrazono)-Δ³-1,3,4-oxadiazoline was prepared as follows:

The carbohydrazone of acetone and p-chlorobenzaldehyde (5.48 g, 0.0217 mol) in methylene chloride (100 ml) was added dropwise, with stirring, over a period of 20 minutes to a solution of lead tetraacetate (14.4 g, 0.0325 mol) in methylene chloride (150 ml) at ice temperature. When addition was complete, the ice bath was removed and the reaction mixture was stirred for one hour. Ice cold water (100 ml) was added, followed by Celite (trademark) to aid in filtration. The solid mass was filtered off and washed with methylene chloride (100 ml). The organic phase was separated and the aqueous layer was extracted twice with 75 ml portions of methylene chloride. The combined methylene chloride phase was washed successively with water, saturated sodium bicarbonate solution, and saturated sodium chloride solution before it was dried with anhydrous sodium sulfate. Evaporation of the solvent with a rotary evaporator left the title compound as a crude yellow solid (4.84 g, 88.8%). Recrystallization from methylene chloride in petroleum ether gave 3.68 g of material melting at 156° to 157.5°. A second recrystallization gave 2.52 g (45%) of pure material (t.l.c.), m.p. 157° to 158° (d), mol. wt., p.m.r. and i.r. in keeping with expectation for the said compound.

Similarly for analogous derivatives:

1. 5,5-Dimethyl-2(p-fluorobenzylidenehydrazono)-Δ³-1,3,4-oxadiazoline: yellow needles, m.p. 120° to 121° (d), 64% (86% initial yield).

2. 5,5-Dimethyl-2-(m-fluorobenzylidenhydrazono)-Δ³-1,3,4-oxadiazoline: yellow needles, m.p. 137° to 138° (d), 68% (88% initial yield).

3. 5,5-Dimethyl-2-(o-fluorobenzylidenehydrazono)-Δ³-1,3,4-oxadiazoline: yellow needles, m.p. 158° to 159° 64% (93% initial yield).

Spectroscopic data proton magnetic resonance Group (1) Ortho-fluoro derivative $CH_3$ : δ 1.66
H : δ 9.05

(2) Meta-fluoro derivative $CH_3$ : δ 1.66
H : δ 8.43

(3) Para-fluoro derivative $CH_3$ : δ 1.67
H : δ 8.46

TABLE 1

2-Hydrazono-Δ³-1,3,4-oxadiazolines[a]

| R₃ | R₁ | R₂ | Melting Point (°C) | %C Calcd. | %C Found | %H Calcd. | %H Found | %N Calcd. | %N Found |
|---|---|---|---|---|---|---|---|---|---|
| H | CH₃ | CH₃ | 95 | 61.10 | 60.95 | 5.59 | 5.78 | 25.91 | 25.90 |
| p-CH₃ | CH₃ | CH₃ | 108–110 | 62.59 | 62.67 | 6.13 | 6.23 | 24.33 | 24.19 |
| H | CH₃ | CH₂CH₃ | 44[b] | — | — | — | — | — | — |
| H | (CH₂)₃ | | Oil[b] | — | — | — | — | — | — |
| H | (CH₂)₄ | | 104 | 64.45 | 64.25 | 5.82 | 5.80 | 23.12 | 23.35 |

[a]Yields were in the range 57 to 78%, based on amounts isolated. Some of the oxidations have been carried out only once and in no case was optimization of the yield attempted.
[b]This low-melting material was not obtained analytically pure. Its n.m.r. and i.r. spectra were consistent with the assigned structure and it gave the expected molecular weight (mass spectrometric).

5,5-Dimethyl-2-(p-methoxybenzylidenehydrazono)-Δ³-1,3,4-oxadiazoline was prepared in 45% yield from the mixed carbohydrazone from anisaldehyde and acetone. m.p. 142°; prominent spectral characteristics as for other members.

5,5-Dimethyl-2-(o-cghlorobenzylidenehydrazono)-Δ³-1,3,4-oxadiazoline was obtained in 68% yield from the carbohydrazone prepared from o-chlorobenzaldehyde and acetone: m.p. 97°.

Other benzylidenehydrazono-oxadiazolines within the scope of the invention have been prepared in a similar manner with appropriate choice of the aldehyde and ketone. Details of five additional compounds prepared are given in Table 1.

All oxadiazolines of the invention absorbed near 1670 cm⁻¹ in the infrared, characteristic of the exocyclic imino function of 2-imino-Δ³-1,3,4-oxadiazolines. The proton n.m.r. spectra included a singlet in the range 1.66 to 1.80 δ from the gem dimethyl group and a low-field singlet (1H) in the range 8.43 to 9.05 δ characteristic of aldimines. Each gave the expected molecular ion in the mass spectrometer and a satisfactory elemental analysis.

The compounds of the invention have analgesic and/or anti-inflammatory activity. For example, the following is a description of the results obtained when 5,5-dimethyl-2-(benzylidenehydrazono)-Δ³-1,3,4-oxadiazoline (A) and 5,5-dimethyl-2-(p-chlorobenzylidenehydrazono)-Δ³-1,3,4-oxadiazoline (B) were submitted to tests designed to detect their biological activity. The substances were administered to animals as a suspension in physiological saline containing Tween 80 (trademark) surfactant.

TOXICITY

Substances were administered intraperitoneally to Swiss albino mice weighing 18 to 22 g.

TABLE 2

| Substance | Dose mg/kg | No. of Animals | % Dead | $LD_{50}$* mg/kg | 95% confidence limits |
|---|---|---|---|---|---|
| A | 128 | 4 | 0 | — | — |
| B | 250 | 10 | 0 | | |
|   | 300 | 10 | 10 | | |
|   | 400 | 10 | 40 | 232 | (218.9 – 245.9) |
|   | 450 | 10 | 50 | | |
|   | 500 | 10 | 100 | | |

ANALGESIC ACTIVITY

Substances were administered subcutaneously to Swiss albino mice weighing 18 to 22 g, before determining their activity in the phenylquinone writhing test (Collier et al. Br. J. Pharmacol. Chemotherap. 32: 295, 1968).

TABLE 3

| Substance | Dose mg/kg | No. of Animals | Response (% inhibition) | $ED_{50}$* mg/kg | 95% confidence limits |
|---|---|---|---|---|---|
| A | 32 | 5 | 40 | | |
|   | 64 | 5 | 56 | 48 | (24.1 – 95.5) |
|   | 128 | 15 | 82 | | |
| B | 16 | 5 | 39 | | |
|   | 32 | 5 | 41 | | |
|   | 64 | 5 | 57 | 45 | (22.5 – 90.0) |
|   | 128 | 5 | 74 | | |
|   | 256 | 5 | 80 | | |

*Determined by the method of Litchfield and Wilcoxon (J. Pharmacol. 96: 99, 1949).

Analgesic activity of substance (B) on inflamed tissue was assessed by the method of Randall and Selitto (Arch. int. pharmacodyn. 111: 409, 1957). The compound was administered subcutaneously to Sprague-Dawley rats weighing 100 to 125 g, half an hour before testing began. Pain threshold was measured 1.5, 2.5 and 4.5 hours later. The change in threshold at 2.5 hours was as follows:

TABLE 4

| Dose mg/kg | No. of Animals | Relative increase in pain threshold % of control |
|---|---|---|
| 16 | 6 | 6.5 |
| 32 | 6 | 32.0 |
| 64 | 6 | 30.0 |
| 128 | 6 | 15.0 |

Application of the Wilcoxon signed rank test (Wilcoxon, F. Biometrics Bull. 1: 80, 1945) showed that at every dose scores of treated animals were statistically different from control animals receiving only physiological saline (P = 0.05 or less).

Analgesic activity of substances (A) and (B) compares with that of aspirin as follows:

TABLE 5

| Test | Compound | $ED_{50}$* mg/kg | 95% confidence limits |
|---|---|---|---|
| Phenylquinone writhing | (A) | 48 | (24.1 – 95.5) |
|  | (B) | 45 | (22.5 – 90.0) |
|  | Aspirin | 52 | (34.6 – 78.0) |
| Inflamed tissue | Aspirin | 35 | (21.8 – 56.0) |

Although not enough compound was available for $ED_{50}$ determination in the inflamed tissue test for substance (B), it is active in a range of concentrations included in the confidence limits of the $ED_{50}$ of aspirin.

We claim:
1. Benzylidenehydrazono-oxadiazoline compounds of the formula:

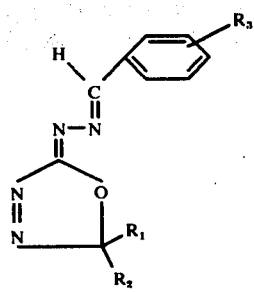

wherein $R_1$ and $R_2$ are both lower alkyl or form with the heterocyclic ring carbon-atom, a cyclopentyl or cyclohexyl ring; and $R_3$ when present is selected from halogen, lower alkyl and lower alkoxy.

2. The compounds of claim 1 wherein $R_1$ and $R_2$ are methyl.

3. The compounds of claim 2 wherein $R_3$ is halogen.

4. The compounds of claim 2 wherein $R_3$ is present and in the para position.

5. The compounds of claim 4 wherein $R_3$ is a chloro group.

6. The compounds of claim 4 wherein $R_3$ is methyl.

7. The compounds of claim 1 in a pharmaceutical carrier, sufficient active compound being present so that the composition has at least one of analgesic and anti-inflammatory activity.

8. The composition of claim 7 wherein a liquid carrier suitable for injection is present.

9. A method preparing compounds as in claim 1 comprising
    a. condensing one of (i) an aldehyde of the formula

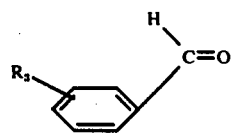

and (ii) a ketone of the formula

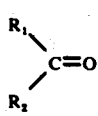

with carbodihydrazide in approximately equimolar amounts, and further condensing the product with the other of (i) and (ii) to form the carbodihydrazone

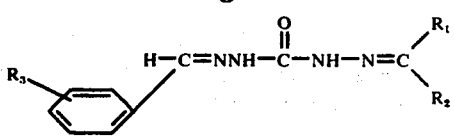

and (b) oxidizing and cyclizing this carbodihydrazone to form oxadiazoline derivatives as in claim 1.

10. The method of claim 9 wherein in step (b) an oxidative cyclizing agent comprised of lead tetraacetate is present.

* * * * *